(12) United States Patent
Liu et al.

(10) Patent No.: US 11,270,447 B2
(45) Date of Patent: Mar. 8, 2022

(54) METHOD FOR IMAGE SEGMENTATION USING CNN

(71) Applicant: Hong Kong Applied Science and Technology Research Institute Company Limited, Hong Kong (CN)

(72) Inventors: Shangping Liu, Hong Kong (CN); Lu Wang, Hong Kong (CN); Pingping Zhang, Dalian (CN); Huchuan Lu, Dalian (CN)

(73) Assignee: Hong Kong Applied Science and Technology Institute Company Limited, Hong Kong (CN)

( * ) Notice: Subject to any disclaimer, the term of this patent is extended or adjusted under 35 U.S.C. 154(b) by 177 days.

(21) Appl. No.: 16/785,784

(22) Filed: Feb. 10, 2020

(65) Prior Publication Data

US 2021/0248761 A1  Aug. 12, 2021

(51) Int. Cl.
*G06T 7/00* (2017.01)
*G06T 7/30* (2017.01)
(Continued)

(52) U.S. Cl.
CPC .............. *G06T 7/30* (2017.01); *G06N 3/0454* (2013.01); *G06N 3/0481* (2013.01); *G06N 3/088* (2013.01);
(Continued)

(58) Field of Classification Search
CPC ............ G06T 7/30; G06T 2207/20084; G06N 3/0454; G06N 3/088; G06N 3/0481; G16H 30/40
See application file for complete search history.

(56) References Cited

U.S. PATENT DOCUMENTS

| 10,095,977 B1 | 10/2018 | Kim et al. |
| 2019/0050667 A1 | 2/2019 | Wang et al. |

(Continued)

FOREIGN PATENT DOCUMENTS

| CN | 109190752 A | 1/2019 |
| CN | 109598732 A | 4/2019 |

(Continued)

OTHER PUBLICATIONS

Liu et al, Efficient Single-Stage Pedestrian Detector by Asymptotic Localization Fitting and Multi-Scale Context Encoding, IEEE Transactions on Image Processing (vol. 29), pp. 1413-1425, Date of Publication: Sep. 16, 2019 (Year: 2019).*

(Continued)

*Primary Examiner* — Ping Y Hsieh
*Assistant Examiner* — Xiao Liu
(74) *Attorney, Agent, or Firm* — S&F/WEHRW

(57) ABSTRACT

In a convolutional neural network (CNN) using an encoder-decoder structure for image segmentation, a multi-scale context aggregation module receives an encoded final-stage feature map from the encoder, and sequentially aggregates multi-scale contexts of this feature map from a global scale to a local scale to strengthen semantic relationships of contexts of different scales to improve segmentation accuracy. The multi-scale contexts are obtained by computing atrous convolution on the feature map for different dilation rates. To reduce computation, a channel-wise feature selection (CFS) module is used in the decoder to merge two input feature maps. Each feature map is processed by a global pooling layer followed by a fully connected layer or a 1×1 convolutional layer to select channels of high activation. By subsequent channel-wise multiplication and elementwise summation, only channels with high activation in both (Continued)

feature maps are preserved and enhanced in the merged feature map.

18 Claims, 6 Drawing Sheets

(51) Int. Cl.
 *G06N 3/04*    (2006.01)
 *G06N 3/08*    (2006.01)
 *G16H 30/40*    (2018.01)
(52) U.S. Cl.
 CPC ... *G16H 30/40* (2018.01); *G06T 2207/20084* (2013.01)

(56) References Cited

U.S. PATENT DOCUMENTS

| | | | | |
|---|---|---|---|---|
| 2021/0201499 | A1* | 7/2021 | Qin | G06N 3/08 |
| 2021/0256657 | A1* | 8/2021 | Meng | G06K 9/4661 |

FOREIGN PATENT DOCUMENTS

| | | |
|---|---|---|
| CN | 109635711 A | 4/2019 |
| CN | 110232670 A | 9/2019 |
| CN | 110378344 A | 10/2019 |

OTHER PUBLICATIONS

International Search Report and Written Opinion of PCT application No. PCT/CN2020/076560 issued from the International Search Authority dated May 27, 2020.

O. Ronneberger, P. Fischer and T. Brox, (2015) in "U-Net: Convolutional Networks for Biomedical Image Segmentation," in: Navab N., Hornegger J., Wells W., Frangi A. (eds) Medical Image Computing and Computer-Assisted Intervention—MICCAI 2015, Lecture Notes in Computer Science, vol. 9351, Springer.

C.-C. Wu, F. A. Wick and M. Pomplun, "Guidance of visual attention by semantic information in real-world scenes," Frontiers in Psychology, vol. 5, article 54, Feb. 2014.

F. Yu and V. Koltun, "Multi-scale context aggregation by dilated convolutions," published as a conference paper at ICLR 2016, arXiv:1511.07122.

K. He et al., "Deep Residual Learning for Image Recognition," in CVPR, 2016.

Y. Liu et al., "Automatic Building Extraction on High-Resolution Remote Sensing Imagery Using Deep Convolutional Encoder-Decoder with Spatial Pyramid Pooling," IEEE Access, vol. 7, pp. 128774-128786, 2019.

K. Yang et al., "PASS: Panoramic Annular Semantic Segmentation," IEEE Transactions on Intelligent Transportation Systems, pp. 1-15, Sep. 2019.

* cited by examiner

METHOD FOR IMAGE SEGMENTATION USING CNN

LIST OF ABBREVIATIONS

2D Two-dimensional
3D Three-dimensional
CFS Channel-wise feature selection
CNN Convolutional neural network
CPU Central processing unit
CT Computed tomography
DS Dice score
FLOP Floating point operation
GP Global pooling
GPU Graphics processing unit
MB Megabyte
MRI Magnetic resonance imaging
OCT Optical coherence tomography
PET Positron emission tomography
TDP Thermal design power

TECHNICAL FIELD

The present disclosure generally relates to image segmentation using a CNN. In particular, the present disclosure relates to a network structure of CNN for improving segmentation accuracy and reducing a computation requirement.

BACKGROUND

Medical image segmentation is concerned with extracting anatomical regions of interest from a medical image or a series of images by an automatic or semi-automatic process. Artificial intelligence is useful to automatic segmentation of medical images. In particular, CNNs, which are configurable to resemble neurological circuits of a human visual system in image understanding, are increasingly deployed in medical image segmentation.

Most of CNN models have been designed for processing nature images. These models, such as PSPNet, Mask RCNN and DeepLabv3+, are large networks each having a large number of parameters. For instance, PSPNet has 66 million parameters and DeepLabv3+ has 41 million parameters. It is difficult to deploy a large network for a cutting-edge medical device, partly because optimization of this device in implementation is usually biased to medical functionalities that are provided rather than computing power. It is even more difficult to implement a large CNN if the cutting-edge medical device is mobile or portable. In addition, it is difficult to train a large network based on a medical dataset with a limited number of training images. For example, datasets used to train DeepLabv3+ include PASCAL VOC 2012 (11540 images) and Cityscapes (5000 images). Medical datasets are tailored for specific clinical imaging situations, such as brain imaging. Furthermore, there are many imaging modalities, such as CT, MR1, X-Ray, ultrasound, microscopy, endoscopy, OCT, dermoscopy, etc. Different modalities lead to the use of different medical datasets for CNN training. It follows that development of medical datasets with a large number segmented images for CNN training are often not easy.

Although lightweight networks, such as ENet, ESPNet and Fast-SCNN, have been designed for use in mobile computing devices, segmentation accuracies achieved by these networks are often not high enough for most medical applications. U-Net has been designed for segmenting biomedical images and is relatively lightweight, but it also suffers from the same problem of segmentation accuracy. The segmentation accuracy of U-Net still needs to be improved for satisfying segmentation-accuracy requirements of most medical applications. Most of extensions and modifications to U-Net have been made for improving the accuracy, but it leads to a large additional computation cost. For example, the amount of computation required by U-Net++ is 2.5 times more than that required by U-Net.

There is a need in the art for a lightweight CNN model improved over U-Net in segmentation accuracy while maintaining or even reducing a computation requirement as compared to U-Net. Although this lightweight CNN model is particularly advantageous for medical image segmentation, it is expected this CNN model is also useful to segmenting images other than medical images.

SUMMARY

The present disclosure provides a first computer-implemented method for segmenting an input image into a segmentation map. The method comprises the step of running a CNN to generate the segmentation map from the input image after the CNN is trained.

The CNN comprises an encoder, a multi-scale context aggregation module, and a decoder. The encoder is arranged to encode the input image into an encoded final-stage feature map through plural encoding stages, generating one or more encoded intermediate feature maps before the encoded final-stage feature map is generated. The multi-scale context aggregation module is used for improving segmentation accuracy over U-Net. The multi-scale context aggregation module is arranged to sequentially aggregate multi-scale contexts of the encoded final-stage feature map from a global scale to a local scale for allowing semantic relationships of respective contexts of different scales to be strengthened to thereby improve segmentation accuracy. An aggregated-context feature map is thereby generated by the multi-scale context aggregation module. The decoder is arranged to decode the aggregated-context feature map according to, directly or indirectly, the encoded final-stage feature map and the one or more encoded intermediate feature maps, whereby the segmentation map is generated.

The multi-scale context aggregation module is further arranged to compute a plurality of atrous-convolution feature maps of the encoded final-stage feature map, and to compute the aggregated-context feature map from the plurality of atrous-convolution feature maps. In particular, N atrous-convolution feature maps of the encoded final-stage feature map are computed for N different dilation rates, respectively, for extracting the multi-scale contexts from the encoded final-stage feature maps, where N≥2. The aggregated-context feature map, $s_N$, is computed by a recursive procedure of computing $s_n = f_n(r_n \oplus s_{n-1})$ for $n \in \{1, 2, \ldots, N\}$ where $r_n$ is an nth computed atrous-convolution feature map, $s_n$ is an nth intermediate result of the aggregated-context feature map, $s_0$ is a null feature map, $\oplus$ denotes elementwise summation and $f_n$ is an nth nonlinear function. In addition, $(r_1, r_2, \ldots, r_N)$ forms a sequence of atrous-convolution feature maps arranged in a descending order of dilation rate such that in the computation of the aggregated-context feature map, local-scale contexts of the encoded final-stage feature map are allowed to be aggregated under guidance of global-scale contexts thereof. The nonlinear functions $f_1$, $f_2, \ldots, f_N$ are independently configured.

Preferably, $f_n$ is given by $f_n(x) = x + g_n(x)$ where x denotes an input feature map, $f_n(x)$ denotes an output of the nth nonlinear function with the input feature map, and $g_n(x)$ is a nonlinear component of $f_n(x)$. The multi-scale context aggregation module may include a plurality of bottleneck blocks for computing $f_1, f_2, \ldots, f_N$. An individual bottleneck block may include one or more convolutional layers.

The decoder comprises a plurality of decoding stages. An individual decoding stage is arranged to receive first and second input feature maps to generate one output map. The first and second input feature maps each have a same dimension and a same number of channels. The individual decoding stage comprises a merging module and a decoding block. The merging module is arranged to merge the first and second input feature maps to form a merged feature map. The decoding block is arranged to decode the merged feature map to give the output map.

Preferably, the merging module is a CFS module for reducing a computation requirement. The CFS module is arranged to process the first and second input feature maps each with an individual cascade of a GP layer and an attention layer to yield first and second attention feature maps of dimension 1×1×C, respectively. Each of the first and second input feature maps has a dimension of W×H×C. The GP layer performs a pooling operation on W×H data in each of C channels of a respective input feature map to yield a GP-output feature map of dimension 1×1×C. The attention layer generates a respective attention feature map by determining an attention of each of the C channels according to the GP-output feature map such that a channel of higher activation among the C channels has a higher attention. The attention layer is either a fully connected layer or a 1×1 convolutional layer. A same set of weights is used in the attention layer of the individual cascade in processing both the first and second input feature maps. The CFS module is further arranged to: channel-wise multiply the first input feature map with the second attention feature map to yield a first post-processed input feature map; channel-wise multiply the second input feature map with the first attention feature map to yield a second post-processed input feature map; and perform elementwise addition of the first and second post-processed input feature maps to give the merged feature map such that channels with high activation in both the first and second input feature maps are preserved and enhanced.

In certain embodiments, the pooling operation is either a first operation of computing an average value or a second operation of finding a maximum value.

In certain embodiments, the attention layer employs a sigmoid function as an activation function.

In certain embodiments, each data in the respective attention feature map is in a range of 0 and 1.

The plurality of decoding stages comprises an initial decoding stage and one or more subsequent decoding stages. The one or more subsequent decoding stages include a last decoding stage. The first input feature map of the initial decoding stage is the aggregated-context feature map, and the second input feature map thereof is, or is derived from, the encoded final-stage feature map. The first input feature map of an individual subsequent decoding stage is the output map of a decoding stage immediately preceding the individual subsequent decoding stage, and the second input feature map thereof is, or is derived from, a feature map selected from the one or more encoded intermediate feature maps. The output map of the last decoding stage is the segmentation map. In certain embodiments, the decoding block of the individual decoding stage includes one or more convolutional layers. The decoding block of the last decoding stage is realized as a 1×1 convolutional layer.

Optionally, the CNN further comprises one or more 1×1 convolutional layers. An individual 1×1 convolutional layer is arranged to derive the second input feature map of a decoding stage selected from the plurality of decoding stages. The second input feature map of the selected decoding stage is derived from a corresponding feature map generated by the encoder by resampling the corresponding feature map such that the first and second input feature maps of the selected decoding stage have a same dimension.

In certain embodiments, an individual encoding stage includes one or more convolutional layers.

The present disclosure also provides a second computer-implemented method for segmenting an input image into a segmentation map. The method comprises the step of running a CNN to generate the segmentation map from the input image after the CNN is trained.

The CNN comprises an encoder and a decoder. The encoder is arranged to encode the input image into an encoded final-stage feature map through plural encoding stages, generating one or more encoded intermediate feature maps before the encoded final-stage feature map is generated. The decoder is arranged to decode the encoded final-stage feature map according to, directly or indirectly, the one or more encoded intermediate feature maps, whereby the segmentation map is generated. The decoder comprises a plurality of decoding stages. An individual decoding stage is arranged to receive first and second input feature maps to generate one output map. The first and second input feature maps each have a same dimension and a same number of channels. The individual decoding stage comprises a merging module and a decoding block. The merging module is arranged to merge the first and second input feature maps to form a merged feature map. The decoding block is arranged to decode the merged feature map to give the output map. The merging module is any of the embodiments of the CFS module as disclosed above for the first computer-implemented method.

The plurality of decoding stages comprises an initial decoding stage and one or more subsequent decoding stages. The one or more subsequent decoding stages include a last decoding stage. The first input feature map of the initial decoding stage is the encoded final-stage feature map. The first input feature map of an individual subsequent decoding stage is the output map of a decoding stage immediately preceding the individual subsequent decoding stage. The second input feature map of an individual decoding stage is, or is derived from, a feature map selected from the one or more encoded intermediate feature maps. The output map of the last decoding stage is the segmentation map. In certain embodiments, the decoding block of the individual decoding stage includes one or more convolutional layers. The decoding block of the last decoding stage is realized as a 1×1 convolutional layer.

Optionally, the CNN further comprises one or more 1×1 convolutional layers. An individual 1×1 convolutional layer is arranged to derive the second input feature map of a decoding stage selected from the plurality of decoding stages. The second input feature map of the selected decoding stage is derived from a corresponding feature map generated by the encoder by resampling the corresponding feature map such that the first and second input feature maps of the selected decoding stage have a same dimension.

In certain embodiments, an individual encoding stage includes one or more convolutional layers.

Other aspects of the present disclosure are disclosed as illustrated by the embodiments hereinafter.

DETAILED DESCRIPTION

A CNN is a neural network having plural hidden layers at least some of which are convolutional layers, where each convolutional layer is used to perform a convolution or dot product with an input provided to the layer. The CNN is implemented and run by a computing device programmed with program codes for performing data operations according to a network structure of the CNN.

Disclosed herein is a CNN model for improving a segmentation performance of medical images over U-Net while maintaining or reducing a computation requirement as compared to U-Net. Specifically, the CNN model employs a multi-scale context aggregation module for achieving a first goal of improving the segmentation performance, and a CFS module for reducing the computation requirement.

Figure 1:
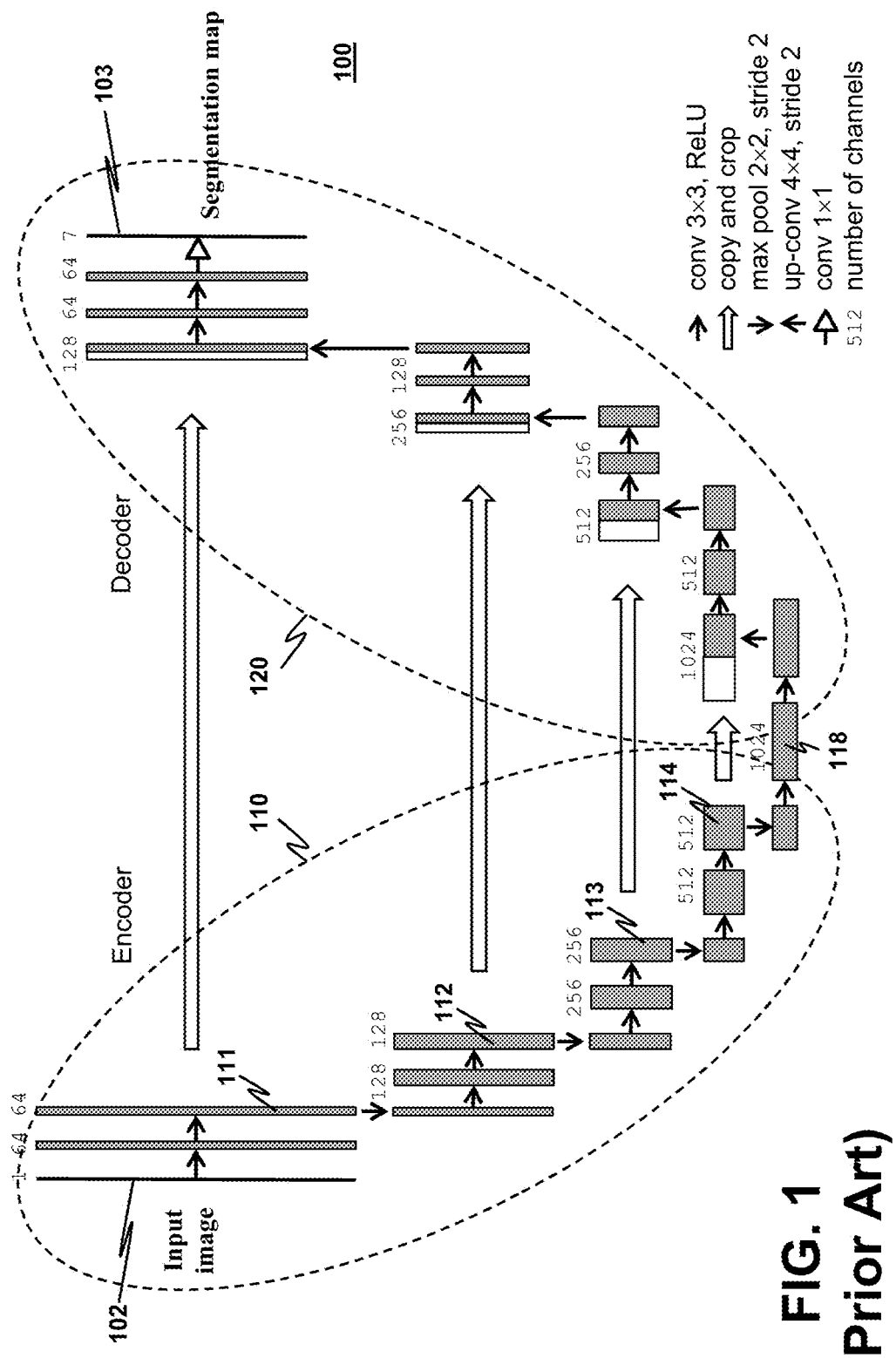
FIG. 1 depicts a structure of U-Net.

Before the disclosed CNN model is elaborated, an overview of U-Net is provided as follows. U-Net was proposed by O. RONNEBERGER, P. FISCHER and T. BROX, (2015) in "U-Net: Convolutional Networks for Biomedical Image Segmentation," in: Navab N., Hornegger J., Wells W., Frangi A. (eds) Medical Image Computing and Computer-Assisted Intervention—MICCAI 2015, *Lecture Notes in Computer Science*, vol. 9351, Springer, the disclosure of which is incorporated by reference herein. FIG. 1 depicts a structure of U-Net. U-Net employs an encoder-decoder structure 100. An input image 102 is processed by an encoder 110 to generate high-dimensional features via convolution and down-sampling. A main output of the encoder 110 is a multi-channel feature map 118 containing the generated high-dimensional features. The encoder 110 processes the input image 102 through multiple encoding stages. The final encoding stage yields the feature map 118, which can be referred to as an encoded final-stage feature map. Each of previous encoding stages yields an encoded intermediate feature map. As shown in FIG. 1, there are four encoded intermediate feature maps 111-114. Each of the encoded intermediate feature maps 111-114 is multi-channel. Note that, as an example for illustration, the encoded intermediate feature map 111 has a lower number of channels than another encoded intermediate feature map 114, which has gone through more number of encoding stages. It indicates that an encoded intermediate feature map becomes more feature-rich after passing through more encoding stages. The encoded final-stage feature map 118 is the richest in feature. A decoder 120 takes the high-dimensional features in the encoded final-stage feature map 118 and generates therefrom an output segmentation map 103 via convolution and up-sampling. The decoder 120 has multiple decoding stages. The encoded intermediate feature maps 111-114, generated by the encoder 110, are also used by the decoder 120 during various decoding stages to generate the output segmentation map 103.

The CNN model disclosed herein is illustrated as follows with the aid of FIG. 2, which depicts an exemplary CNN model 200 for segmenting an input image 202 into a segmentation map 203.

Similar to U-Net, the CNN model 200 employs an encoder-decoder structure for segmenting the input image 202. The CNN model 200 comprises an encoder 210 and a decoder 260. Advantageously, the CNN model 200 further comprises a multi-scale context aggregation module 250 for further processing an encoded final-stage feature map 215-M generated by the encoder 210 instead of allowing the encoded final-stage feature map 215-M to be directly decoded by the decoder 260.

The encoder 210 is arranged to encode the input image 202 into the encoded final-stage feature map 215-M through plural encoding stages (realized as M encoding blocks 211-1:M), generating one or more encoded intermediate feature maps 215-14M−1) before the encoded final-stage feature map 215-M is generated. The one or more encoded intermediate feature maps 215-1:(M−1) and the encoded final-stage feature map 215-M collectively form a plurality of feature maps 215-1:M generated by the encoder 210. As the encoding stages are realized as M encoding blocks 211-1:M where M≥2, there are M encoding stages in the encoder 210. Similar to U-Net, each of the encoding blocks 211-1:M usually comprises one or more convolutional layers. Furthermore, down-sampling may be used in one or more of the encoding blocks 211-1:M for feature map generation. Methods of down-sampling include max pooling and convolution subsampling.

The encoded final-stage feature map 215-M contains contextual information. Large-scale or global-scale contextual information contains more semantics whereas small-scale or local-scale contextual information contains more geometric details. The encoded final-stage feature map 215-M is decomposable into multiple-scale contexts, which include both large-scale contexts and small-scale contexts. In a human visual system, an image is analyzed in a neurological circuit by using global prior information to guide understanding local features. See, for example, a review article of C.-C. WU, F. A. WICK and M. POMPLUN, "Guidance of visual attention by semantic information in real-world scenes," *Frontiers in Psychology*, vol. 5, article 54, February 2014, the disclosure of which is incorporated by reference herein. By considering relationships among the multi-scale contexts, i.e. semantic gap and global guidance, it is advantageous to sequentially aggregate contextual information from global-scale contexts to local-scale contexts such that using the resultant aggregated-context information for segmentation has potential to increase segmentation accuracy over directly using the encoded final-stage feature map 215-M. The multi-scale context aggregation module 250 is developed based on the aforementioned observation.

The multi-scale context aggregation module 250 is arranged to sequentially aggregate multi-scale contexts of the encoded final-stage feature map 215-M from a global scale to a local scale for allowing semantic relationships of respective contexts of different scales to be strengthened. The multi-scale context aggregation module 250 generates an aggregated-context feature map 255 as an output. Advantageously, the multi-scale context aggregation module 250 is configurable. By strengthening the semantic relationships among the multi-scale contexts according to the human visual mechanism, the resultant segmentation accuracy is improved by using the aggregated-context feature map 255 over directly using the encoded final-stage feature map 215-M in decoding.

The decoder 260 is arranged to decode the aggregated-context feature map 255 according to, directly or indirectly, the encoded final-stage feature map 215-M and the one or more encoded intermediate feature maps 215-1:(M−1). The segmentation map 203 is generated by the decoder 260.

Figure 3:
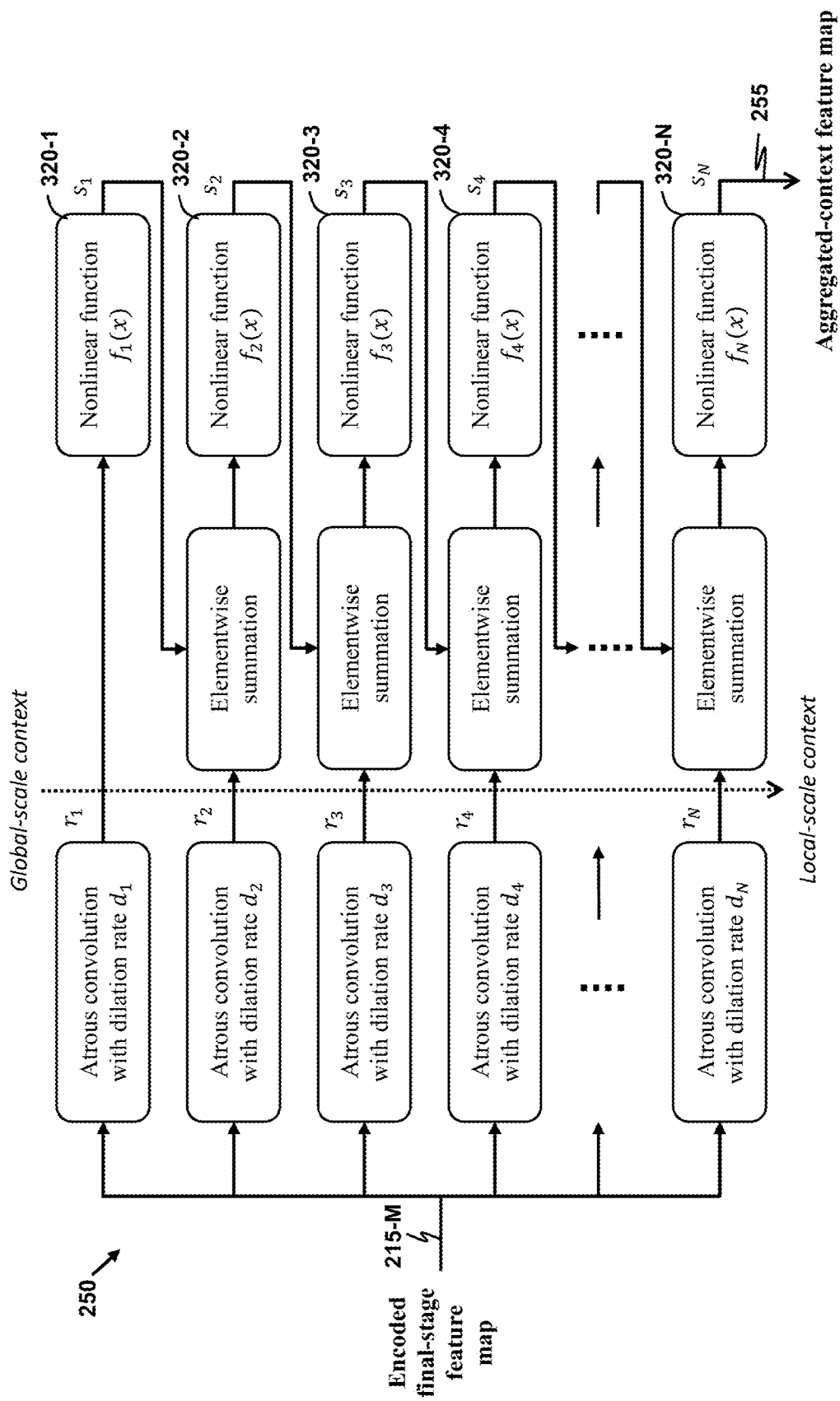
FIG. 3 depicts an exemplary schematic diagram of a multi-scale context aggregation module of the CNN model.

FIG. 3 depicts an exemplary schematic diagram of the multi-scale context aggregation module 250.

In the multi-scale context aggregation module 250, the multi-scale contexts are extracted from the encoded final-stage feature map 215-M by taking atrous convolution on the encoded final-stage feature map 215-M under different dilation rates. Atrous convolution is also known as dilated convolution. Details of atrous convolution and mathematical formulas thereof are available in the art, for example: F. YU and V. KOLTUN, "Multi-scale context aggregation by dilated convolutions," published as a conference paper at ICLR 2016, arXiv:1511.07122, the disclosure of which is incorporated by reference herein. The dilation rate, also known as the dilation factor, is a parameter used in computing atrous convolution. Larger-scale contexts are obtained by taking atrous convolution with a larger dilation rate. Conversely, taking atrous convolution under a smaller dilation rate yields smaller-scale contexts. One major advantage of atrous convolution over other techniques of extracting multi-scale contextual information is that exponential expansion of the receptive field is supported without loss of resolution or coverage. Another major advantage of atrous convolution is that only a small amount of computation is required to generate a larger-scale context. For example, a 3×3 kernel with a dilation rate of 9 has the same field of view as a 19×19 kernel. The multi-scale context aggregation module 250 is arranged to take N instances of atrous convolution on the encoded final-stage feature map 215-M with N different dilation rates, $d_1, d_2, \ldots, d_N$, where N≥2 and $d_1 > d_2 > \ldots > d_N$. It yields $r_1, r_2, \ldots, r_N$ where $r_n$ is an nth atrous-convolution feature map. The largest dilation rate $d_1$ is selected to be sufficiently large, e.g., 9 and 17, so as to extract the global-scale contexts. Usually, the smallest dilation rate $d_N$ is selected to be 1 for extracting the local-scale contexts. In general, the dilation rates are determined by the size of features in the encoded final-stage feature map 215-M. Note that $(r_1, r_2, \ldots, r_N)$ forms a sequence of atrous-convolution feature maps arranged in a descending order of dilation rate, or equivalently from the global-scale contexts to the local-scale contexts.

As mentioned above, the aggregated-context feature map 255 is obtained by sequential aggregation of contextual information from the global-scale contexts to the local-scale contexts. Specifically, the aggregated-context feature map 255 is computed from $r_1, r_2, \ldots, r_N$ by a recursive procedure $s_n = f_n(r_n \oplus s_{n-1})$ for $n \in \{1, 2, \ldots, N\}$ where $s_N$ is the aggregated-context feature map 255, $s_n$ is an nth intermediate result of the aggregated-context feature map 255, $s_0$ is initialized as a null feature map, $\oplus$ denotes elementwise summation, and $f_n$ is an nth nonlinear function. Note that $s_{n-1}$ represents a nonlinear aggregation of contextual information from $r_1$ to $r_{n-1}$. Since $r_1, r_2, \ldots, r_N$ are arranged in a descending order of dilation rate, or equivalently from the global scale to the local scale, contextual information in $r_n$ is of a scale smaller than any scale of contextual information present in $s_{n-1}$. Elementwise summation of $r_n$ and $s_{n-1}$ implies that new contextual information of a smaller scale is added to $s_{n-1}$. As $r_1, r_2, \ldots, r_N$ are arranged from the global scale to the local scale, it follows that the local-scale contexts of the encoded final-stage feature map 215-M are allowed to be aggregated under guidance of the global-scale contexts thereof. The nonlinear functions $f_1, f_2, \ldots, f_N$ are independently configured. The multi-scale context aggregation module 250 introduces more complicated nonlinear operations (as multiple nonlinear functions used). As a result, it has a stronger capacity to model the relationships of different contexts than simple convolution operations.

Advantages of the multi-scale context aggregation module 250 employing atrous convolution and recursive computation of the aggregated-context feature map 255 are summarized as follows. First, enhanced deep features are incorporated to help improve the segmentation accuracy. Second, global-to-local aggregation reduces semantic gaps among contexts with different scales, resulting in smooth predictions. Third, local features are progressively integrated in a residual refinement manner, effectively helping end-to-end training.

Preferably, the nonlinear function $f_n$ is selected to be $f_n(x)=x+g_n(x)$ where x denotes an input feature map, $f_n(x)$ denotes an output of the nth nonlinear function with the input feature map, and $g_n(x)$ is a nonlinear component of $f_n(x)$. This choice of $f_n$ avoids an undesirable situation that contextual information contained in $r_n \oplus s_{n-1}$ is destroyed or distorted due to an ill-trained nonlinear function. In addition, each of the nonlinear functions $f_1, f_2, \ldots, f_N$ modeled by $f_n(x)=x+g_n(x)$ may be computed by a bottleneck block of ResNet. For a description of the bottleneck block, see K. H E et al., "Deep Residual Learning for Image Recognition," in CVPR, 2016, the disclosure of which is incorporated by reference herein. It is preferable that the multi-scale context aggregation module 250 includes a plurality of bottleneck blocks 320-1:N for computing $f_1, f_2, \ldots, f_N$. Each of the bottleneck blocks 320-1:N can be realized with one or more convolutional layers.

Figure 2:
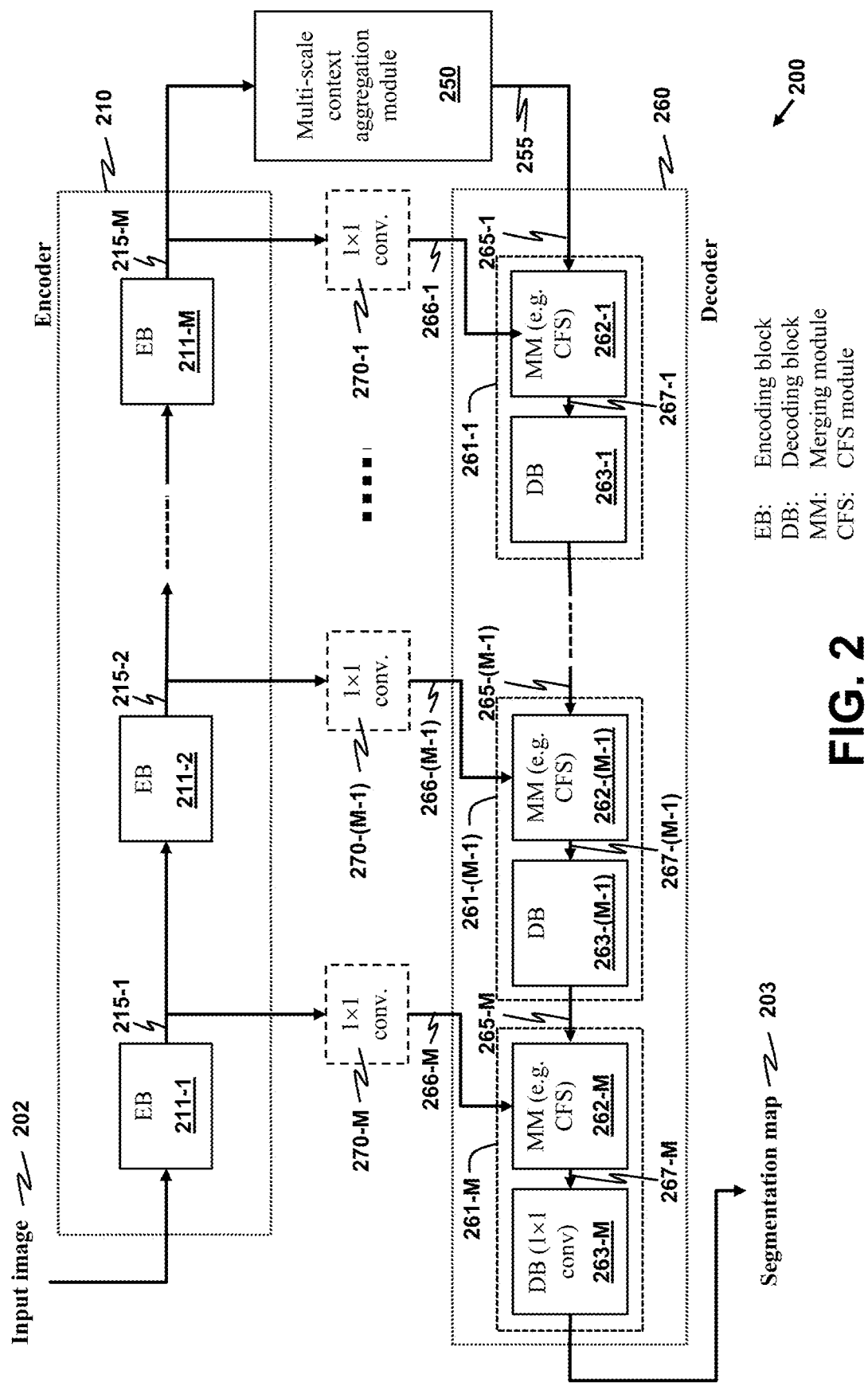
FIG. 2 depicts an exemplary CNN model, which includes a multi-scale context aggregation module for improving segmentation accuracy, and, preferably, CFS modules for reducing a computation requirement.

Refer to FIG. 2. The decoder 260 comprises a plurality of decoding stages 261-1:M. In the description hereinafter, m is considered to be m∈{1,2, ... M} unless otherwise specified. An individual decoding stage 261-m is arranged to receive a first input feature map 265-m and a second input feature map 266-m to generate an output map. Each of the first and second input feature maps 265-m, 266-m has a same dimension and a same number of channels. The individual decoding stage 261-m comprises a merging module 262-m and a decoding block 263-m. The merging module 262-m is arranged to merge the first and second input feature maps 265-m, 266-m to form a merged feature map 267-m. The decoding block 263-m is arranged to decode the merged feature map 267-m to give the output map.

The plurality of decoding stages 261-1:M comprises an initial decoding stage 261-1 and one or more subsequent decoding stages 261-2:M. The one or more subsequent decoding stages 261-2:M includes a last decoding stage 261-M. The output map of the last decoding stage 261-M is the segmentation map 203.

The first input feature map 265-1 of the initial decoding stage 261-1 is the aggregated-context feature map 255. The second input feature map 266-1 of the initial decoding stage 261-1 is, or is derived from, the encoded final-stage feature map 215-M.

The first input feature map 265-m' of an individual subsequent decoding stage 261-m' is the output map of a decoding stage 261-(m'-1) immediately preceding the individual subsequent decoding stage 261-m', where m'∈ {2,3, ..., M}. The second input feature map 266-m' of the decoding stage 261-m' is, or is derived from, a feature map selected from the one or more encoded intermediate feature maps 215-1:(M−1).

Optionally, the CNN model 200 further comprises one or more 1×1 convolutional layers 270-1:M. Since the first and second input feature maps 265-m, 266-m received by the individual decoding stage 261-m are required to have the same dimension, and since a corresponding feature map generated by the encoder 210 and used by the merging block 262-m may not match the dimension of the first input feature map 265-m, one of the 1×1 convolutional layers 270-1:M may be used to resample the aforementioned corresponding feature map to derive the second input feature map 266-m such that the first and second input feature maps 265-m, 266-m have the same dimension.

The decoding block 263-m of the individual decoding stage 261-m includes one or more convolutional layers. In particular, the decoding block 263-M of the last decoding stage 261-M is realized as a 1×1 convolutional layer.

The merging block 262-m may be implemented by an arrangement similar to U-Net. That is, the merging block 262-m may be arranged to concatenate the first and second input feature maps 265-m, 266-m to form an expanded feature map (with a higher number of channels than each of the two input feature maps 265-m, 266-m) followed by applying a convolutional layer to condense the expanded feature map into the merged feature map 267-m where the merged feature map 267-m has a smaller number channels than the expanded feature map. However, this arrangement involves a lot of computation. To reduce the amount of computation, a CFS module as disclosed herein is advantageously used for realizing the merging block 262-m.

Figure 4:
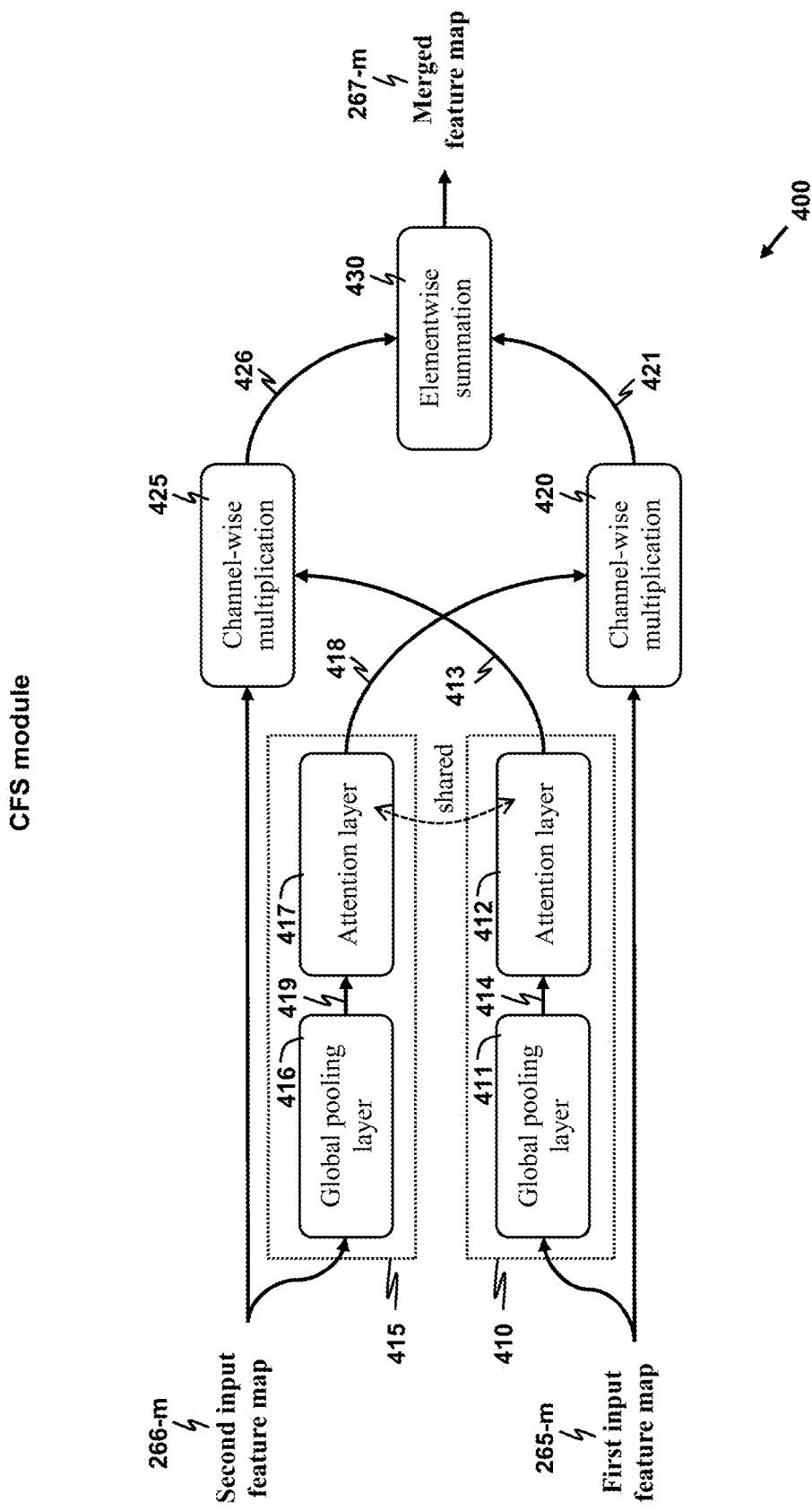
FIG. 4 depicts a schematic diagram of an exemplary CFS module used as a merging block of the CNN model.

FIG. 4 depicts a schematic diagram of an exemplary CFS module 400 for receiving the first and second input feature maps 265-m, 266-m to generate the merged feature map 267-m.

In the CFS module 400, the first input feature map 265-m is processed by a first cascade 410 of a first GP layer 411 and a first attention layer 412 to yield a first attention feature map 413. Similarly, the second input feature map 266-m is processed by a second cascade 415 of a second GP layer 416 and a second attention layer 417 to yield a second attention feature map 418. For illustration, consider that each of the first and second input feature maps 265-m, 266-m has a dimension of W×H×C. Each of the first and second attention feature maps 413, 418 has a dimension of 1×1×C.

In the first cascade 410, the first GP layer 411 performs a pooling operation on W×H data in each of C channels of the first input feature map 265-m to yield a first GP-output feature map 414 of dimension 1×1×C. The first attention layer 412 generates the first attention feature map 413 by determining an attention of each of the C channels according to the first GP-output feature map 414 such that a channel of higher activation among the C channels has a higher attention. That a channel has high activation means that a large amount of information is contained in the channel and is intended to be passed from, e.g., one layer to the next. Thus, a channel having high activation is given a higher attention. The first attention feature map 413 contains rich semantic information of the first input feature map 265-m. If the value for the ith channel given by the first attention feature map 413 is large, it indicates that the ith channel has high activation, so that the first input feature map 265-m contains the semantic represented by the ith channel.

The first and second cascade 410, 415 performs a similar function. In the second cascade 415, the second GP layer 416 performs a pooling operation on W×H data in each of C channels of the second input feature map 266-m to yield a second GP-output feature map 419 of dimension 1×1×C. The second attention layer 417 generates the second attention feature map 418 by determining an attention of each of the C channels according to the second GP-output feature map 419 such that a channel of higher activation among the C channels has a higher attention. Similarly, the second attention feature map 418 contains rich semantic information of the second input feature map 266-m. If the value for the ith channel given by the second attention feature map 418 is large, it indicates that the ith channel has high activation, so that the second input feature map 266-m contains the semantic represented by the ith channel.

Note that the same pooling operation is implemented in each of the first and second GP layers 411, 416 such that the first and second input feature maps 265-m, 266-m are processed with the same pooling operation. In general, the pooling operation of the respective GP layer may be selected to be one of generalized pooling functions. Usually and conveniently, the pooling operation is selected to be either a first operation of computing an average value, or a second operation of finding a maximum value.

Each of the attention layers 412, 417 is either a fully connected layer or a 1×1 convolutional layer. It follows that the first and second attention feature maps 413, 418 are of dimension 1×1×C. Advantageously and preferably, each of the attention layers 412, 417 employs a sigmoid function as an activation function. The sigmoid function utilizes attentions for retaining or removing semantic information. A choice of the sigmoid function, S(x), is given by $S(x)=1/(1+\exp(-x))$. By using this choice of S(x), or an appropriate activation function, a data value in the first or second attention feature maps 413, 418 is in the range of 0 and 1. Furthermore, the first and second attention layers 412, 417 are shared such that a same set of weights is used in the two attention layers 412, 417 in processing the first and second input feature maps 265-m, 266-m.

The CFS module 400 is further arranged to channel-wise multiply the first input feature map 265-m with the second attention feature map 418 (as indicated by channel-wise multiplication 420). A first post-processed input feature map 421 is thereby obtained. Similarly, the CFS module 400 is additionally arranged to channel-wise multiply the second input feature map 266-m with the first attention feature map 413 (as indicated by channel-wise multiplication 425). A second post-processed input feature map 426 is thereby obtained. Note that the first and second input feature maps 265-m, 266-m are cross-processed with the second and first attention feature maps 418, 413, respectively. The reason is to achieve a desirable result that channels with high activation in both the first and second input feature maps 265-m, 266-m are preserved and enhanced. This desirable result is achieved by additionally performing elementwise addition 430 of the first and second post-processed input feature maps 421, 426. The summation gives the merged feature map 267-m.

In summary, y, the merged feature map 267-m, is computed by $y=(x_1 \otimes (DM(GP(x_2)))) \oplus (x_2 \otimes (DM(GP(x_1))))$ where: $x_1$ is the first input feature map 265-m; $x_2$ is the second input feature map 266-m; GP(•) is the global pooling operation; DM(•) is the attention operation realized by a (shared) fully connected layer or a 1×1 convolution layer; ⊗ denotes channel-wise multiplication; and ⊕ denotes elementwise summation.

Figure 5:
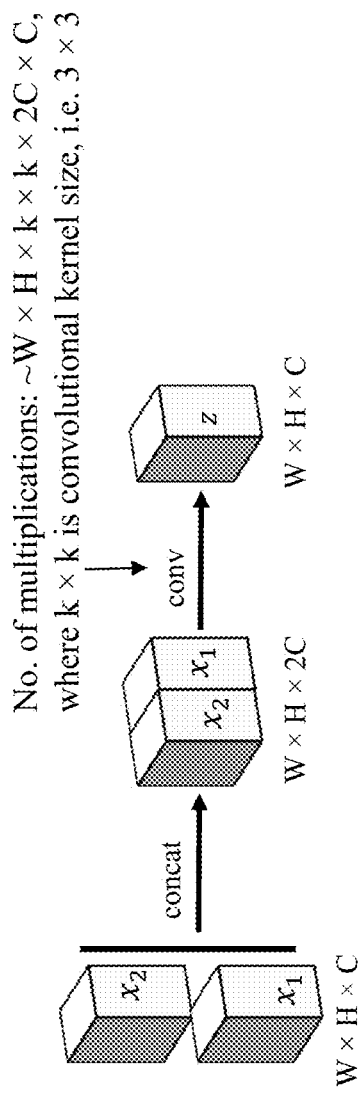
FIG. 5 depicts a conventional merging scheme as used by U-Net and a merging scheme based on the CFS module for comparison of the two schemes in number of multiplications.
Figure 5:
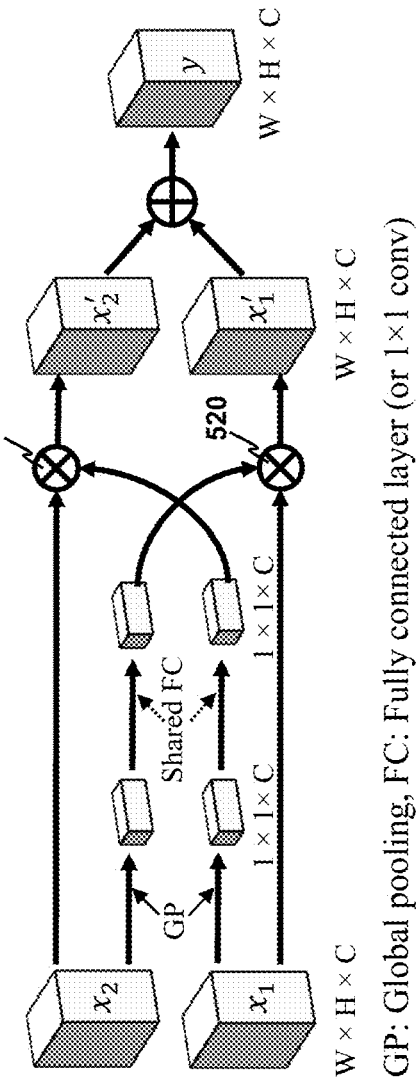

A comparison in number of multiplications required by a conventional merging arrangement (as used in U-Net) and by the CFS module 400 is made. FIG. 5 depicts a conventional merging scheme and a merging operation based on the CFS module 400 for merging two input feature maps $x_1$ and $x_2$ each of dimension W×H×C. For the conventional merging scheme, the number of multiplications required is about W×H×k×k×2C×C where k×k is a convolutional kernel size. Usually, a 3×3 kernel size is used in practice. For the CFS module-based merging scheme, it is first noticed that the two GP layers require a negligible number of multiplications in performing the pooling operation of taking an average value or finding a maximum value on $x_1$ and $x_2$. Furthermore, the two fully connected or convolutional layers operate on feature maps of dimension 1×1×C. The number of multiplications required by these two layers is also negligible. The two channel-wise multiplication operators 520, 525 involve ~2×W×H×C multiplications. In short, the CFS module 400 is only required to compute a small number of multiplications in merging $x_1$ and $x_2$. A significant reduction of computation is achieved by using the CFS module 400.

Table 1 lists the numbers of FLOPs required for the conventional merging arrangement and the CFS module-based merging scheme under input feature maps of size 64×64 and of different numbers of channels. Table 2 compares the FLOPs of the CNN model 200 implemented with the CFS module 400.

TABLE 1

Comparison in FLOPs for input feature maps of size 64 × 64.

| No. of channels | Conventional (GFLOP) | CFS module-based (GFLOP) |
| --- | --- | --- |
| 64 | 0.3 | 0.001 |
| 128 | 1.2 | 0.003 |
| 256 | 4.8 | 0.005 |
| 512 | 19.3 | 0.01 |
| 1024 | 77.3 | 0.02 |

TABLE 2

Comparison in FLOPs for the disclosed CNN model with conventional merging arrangement and with CFS module.

| Image size | Conventional (GFLOP) | CFS module-based (GFLOP) |
| --- | --- | --- |
| 64 × 64 | 1.9 | 0.9 |
| 128 × 128 | 7.9 | 4.0 |
| 256 × 256 | 32.8 | 17.2 |
| 512 × 512 | 136.0 | 74.8 |
| 1024 × 1024 | 563.3 | 314.4 |

The results of Table 1 show that the CFS module 400 achieves a large reduction in required computation. In Table 2, it is shown that a reduction of ~45% in FLOPs is achieved by the disclosed CNN model implemented with the CFS module 400 in comparison to the model without the CFS module Experiments were conducted for demonstrating an improvement in the segmentation accuracy and a reduction in computation requirement over U-Net by using a prototype CNN (abbreviated as CNNp) that adopted the CNN model 200 with the multi-scale context aggregation module 250 and with each of the merging blocks 262-1:M realized by the CFS module 400. The CNNp and U-Net used in the experiments had the same configuration, i.e. using same numbers of encoding and decoding blocks and using the same number of convolutional kernels for each encoding/decoding block. Medical datasets, listed in Table 3, were respectively used in training CNNp and U-Net. Note that GLOM_SEG and GBM_SEG, which are private datasets, are small training datasets whereas KiTs19 and LITS17 are large ones.

TABLE 3

Datasets used in the experiment.

| No. | Modality | Dataset | Task | No. of images | Image size |
| --- | --- | --- | --- | --- | --- |
| 1 | Endoscopy | CVC Colon DB | polyp | 612 | 384 × 288 |
| 2 | Dermoscopy | ISIC 2018 | skin lesion | 2596 | Variant |
| 3 | Light Microscopy | GLOM_SEG* | glomeruli | 525 | 256 × 256 |
| 4 | Electron Microscopy | GBM_SEG* | basement membrane | 200 | 2048 × 2048 |
| 5 | CT | KiTs19 | kidney | 24338 | 512 × 512 |
| 6 | CT | LITS17 | liver | 19163 | 512 × 512 |

*Non-public, private dataset.

The CNNp and U-Net were separately trained with the training datasets. Based on the training datasets, the segmentation accuracy was checked and measured in terms of mean DS. Table 4 lists the segmentation accuracies (in terms of mean DS) achieved by U-Net and CNNp, and improvement in mean DS (ΔmDS) by using CNNp instead of U-Net.

TABLE 4

Segmentation accuracy.

| No. | Dataset | Mean DS (U-Net) | Mean DS (CNNp) | ΔmDS |
| --- | --- | --- | --- | --- |
| 1 | CVC Colon DB | 81.6 | 85.7 | +4.1 |
| 2 | ISIC 2018 | 83.0 | 87.6 | +4.6 |
| 3 | GLOM_SEG | 89.1 | 92.1 | +3.0 |
| 4 | GBM_SEG | 80.5 | 82.2 | +1.7 |
| 5 | KiTs19 | 95.2 | 97.3 | +2.1 |
| 6 | LITS17 | 94.1 | 96.0 | +1.9 |

It is apparent that CNNp outperforms U-Net in segmentation accuracy for all training datasets, large and small. The improvement in mean DS is at least 3 points for GLOM_SEG, CVC Colon DB and ISIC 2018 (respectively having 525, 612 and 2596 images). It follows that even if a training dataset has a limited number of training images, a significant improvement in segmentation accuracy is achievable by CNNp. In case of GBM_SEG, which is a very small dataset having only 200 training images, CNNp still makes an improvement of 1.7 points over U-Net. The foregoing results demonstrate the performance-improvement advantage provided by the disclosed CNN model for small training datasets having a limited number of training images. For large-dataset cases, i.e. LITS17 and KiTs19, CNNp also makes an improvement of segmentation accuracy over U-Net by about 2 points.

Processing times required by CNNp and U-Net were measured under three computing platforms and under different image sizes. Computing platform 1 (CP1) is a GPU-based platform implemented with Nvidia RTX 2080Ti (with a TDP of 250 W). Computing platform 2 (CP2) is a desktop CPU implemented with Intel i9-9900K (with a TDP of 95 W). Computing platform 3 (CP3) is a laptop CPU implemented with Intel i7-8750H (with a TDP of 45 W). Table 5 lists the processing times consumed by running CNNp and U-Net on the three computing platforms for an image-segmentation task under different input-image sizes.

TABLE 5

Processing times (millisecond).

| Input-image size | CP1 | | CP2 | | CP3 | |
|---|---|---|---|---|---|---|
| | U-Net | CNNp | U-Net | CNNp | U-Net | CNNp |
| 64 × 64 | 0.21 | 0.14 | 6.2 | 3.5 | 12.2 | 9.0 |
| 128 × 128 | 0.75 | 0.63 | 26.1 | 15.3 | 50.3 | 37.4 |
| 256 × 256 | 3.5 | 2.9 | 106.2 | 64.1 | 213.3 | 175.5 |
| 512 × 512 | 14.8 | 12.9 | 454.1 | 285.0 | 1003.0 | 909.1 |

CNNp is 1.3 times faster than U-Net on CP1, 1.6 times faster on CP2 and 1.3 times faster on CP3. The results demonstrate that a reduction in computation time is achievable by using CNNp rather than U-Net.

Lastly, numbers of parameters used in CNNp, U-Net and Deeplabv3+ are compared. The number of parameters is related to the memory space required in implementing a CNN. Cutting-edge medical devices tend to be optimized in space usage, power usage, etc., for advanced functionalities of medical origin, such as non-intrusive sensing, rather than optimized for computing power. It follows that a lower number of parameters is more desirable. Table 6 lists the numbers of parameters used by Deeplabv3+, U-Net and CNNp, and the sizes of memory space used to store these parameters.

TABLE 6

Numbers of parameters (in million) and sizes of memory space required (in megabytes).

| | Deeplabv3+ | U-Net | CNNp |
|---|---|---|---|
| 64 × 64 | 41 | 8 | 10 (41 MB) |
| 128 × 128 | 41 | 8 | 12 |
| 256 × 256 | 41 | 8 | 15 |
| 512 × 512 | 41 (160 MB) | 8 (31 MB) | 17 (69 MB) |

Although CNNp uses more parameters than U-Net, CNNp is still lightweight enough (about 41 MB to 69 MB in memory requirement) for the cutting-edge medical devices.

In the present disclosure, the multi-scale context aggregation module 250 and the CFS module 400 are targeted to improve the segmentation accuracy and to reduce the computation requirement, respectively. These two modules 250, 400 realize different and independent advantages. It is possible to adopt only one of the modules 250, 400 to realize a specific advantage.

In a first implementation of the CNN model 200, the multi-scale context aggregation module 250 is present and each of the merging blocks 262-1:M is realized as the CFS module 400. Both advantages of segmentation accuracy improvement and computation reduction are obtained.

In a second implementation of the CNN model 200, the multi-scale context aggregation module 250 is present for obtaining an improvement in segmentation accuracy. Each of the merging blocks 262-1:M is realized by a conventional merging scheme such as concatenation followed by applying a convolutional layer for channel-size reduction.

Figure 6:
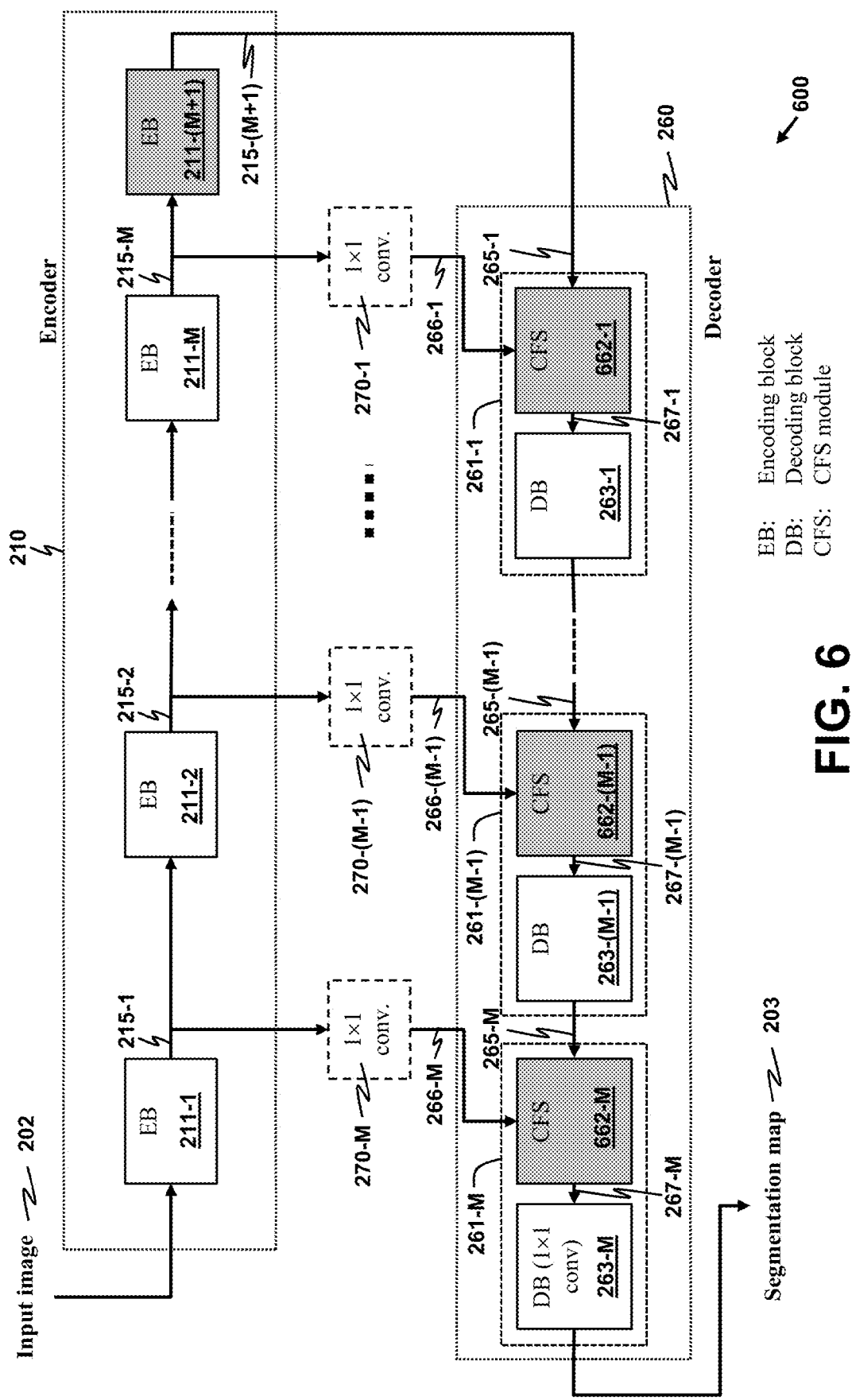
FIG. 6 depicts a modification to the CNN model of FIG. 2 for achieving the computation-reduction advantage.

If it is desired to obtain a computation-reduction advantage for an existing CNN model that uses an encoder-decoder structure, such as U-Net and variants thereof, a modification to the CNN model 200 is required, resulting in a modified CNN model 600 as depicted in FIG. 6. The following modifications are made. First, each of the merging blocks 262-1:M in the CNN model 200 is realized as a copy the CFS module 400, resulting in respective CFS modules 662-1:M in the modified CNN model 600. Second, the multi-scale context aggregation module 250 originally in the CNN model 200 is replaced by an additional encoding block 211-(M+1), an output feature map 215-(M+1) of which is sent to the initial decoding stage 261-1 as its first input feature map 265-1. The additional encoding block 211-(M+1) forms an additional encoding stage in the encoder 210 and is connected to the encoding block 211-M for receiving an input. In this regard, the encoder 210 comprises M+1 encoding blocks 211-1:(M+1) or M+1 encoding stages. The additional encoding block 211-(M+1) becomes an encoded final-stage encoding block. The output feature map 215-(M+1) of the additional encoding block 211-(M+1) becomes an encoded final-stage feature map 215-(M+1) received by the initial decoding stage 261-1 as the first input feature map thereof 265-1. The feature map 215-M, which directly or indirectly forms the second input feature map 266-1 of the initial decoding stage 261-1, becomes an encoded intermediate feature map generated by the encoder 210 in the modified CNN model 600.

An aspect of the present disclosure is to provide a computer-implemented method for segmenting an input image into a segmentation map. The method comprises the step of running a CNN to generate the segmentation map from the input image after the CNN is trained. The method may further comprise the step of training the CNN with labeled images of one or more training datasets. The CNN is realized as any of the embodiments disclosed above for the two CNN models 200, 600.

The input image may be a 2D image or a multi-channel 2D image. The multi-channel 2D image may simply be a color image. The multi-channel 2D image may also be a 3D image formed by a sequence of 2D images. For various diagnostic purposes, 3D scanning of a body part of a patient is required. For example, MRI is widely used in 3D scanning of a brain, and the resultant 3D image composed of many cross-sectional images of the brain imaged at different depths of the head is analyzed for tumor detection. In addition, the multi-channel 2D image often arises in medical imaging in that multiple modalities are used in imaging a body part of a patient under different parameters of operating a scanning means. In one example, when CT and PET are simultaneously used to scan the body part as in PET-CT scanning, a multi-channel image is formed by including one image slice obtained from CT scanning and another one from PET scanning.

Although the disclosed method is particularly advantageous and useful for medical image segmentation, it is not intended that the disclosed method is limited only to the specific case that the input image is a medical image or a 3D medical image. The disclosed method is also usable to segmenting images of non-medical origin while the advantages of the method, such as improved segmentation accuracy and reduced computation requirement, are obtained.

The embodiments disclosed herein may be implemented using computing devices, such as computers, computing servers, general purpose processors, specialized computing processors, digital signal processors, processors specialized in computing convolution products or correlations for images (such as GPUs), programmable logic devices and field programmable gate arrays, where the computing devices are configured or programmed according to the teachings of the present disclosure. Computer instructions or software codes running in the computing devices can readily be prepared by practitioners skilled in the software or electronic art based on the teachings of the present disclosure. The computing devices may be mobile computing devices, such as smartphones, tablets, etc. The computing devices may also be integrated in medical devices used for diagnosis or treatment.

The present disclosure may be embodied in other specific forms without departing from the spirit or essential characteristics thereof. The present embodiment is therefore to be considered in all respects as illustrative and not restrictive. The scope of the invention is indicated by the appended claims rather than by the foregoing description, and all changes that come within the meaning and range of equivalency of the claims are therefore intended to be embraced therein.

What is claimed is:

1. A computer-implemented method for segmenting an input image into a segmentation map, the method comprising the step of running a convolutional neural network (CNN) to generate the segmentation map from the input image after the CNN is trained, wherein:
the CNN comprises:
an encoder arranged to encode the input image into an encoded final-stage feature map through plural encoding stages, generating one or more encoded intermediate feature maps before the encoded final-stage feature map is generated;
a multi-scale context aggregation module arranged to sequentially aggregate multi-scale contexts of the encoded final-stage feature map from a global scale to a local scale for allowing semantic relationships of respective contexts of different scales to be strengthened to thereby improve segmentation accuracy, the multi-scale context aggregation module generating an aggregated-context feature map; and
a decoder arranged to decode the aggregated-context feature map according to, directly or indirectly, the encoded final-stage feature map and the one or more encoded intermediate feature maps, whereby the segmentation map is generated;
the decoder comprises a plurality of decoding stages, an individual decoding stage being arranged to receive first and second input feature maps to generate one output map, the first and second input feature maps each having a same dimension and a same number of channels, wherein the individual decoding stage comprises a merging module and a decoding block, the merging module being arranged to merge the first and second input feature maps to form a merged feature map, the decoding block being arranged to decode the merged feature map to give the output map; and
the merging module is a channel-wise feature selection (CFS) module arranged to:
process the first and second input feature maps each with an individual cascade of a global pooling (GP) layer and an attention layer to yield first and second attention feature maps of dimension 1×1×C, respectively, wherein:
each of the first and second input feature maps has a dimension of W×H×C;
the GP layer performs a pooling operation of W×H data in each of C channels of a respective input feature map to yield a GP-output feature map of dimension 1×1×C; and
the attention layer generates a respective attention feature map by determining an attention of each of the C channels according to the GP-output feature map such that a channel of higher activation among the C channels has a higher attention, the attention layer being either a fully connected layer or a 1×1 convolutional layer, a same set of weights being used in the attention layer of the individual cascade in processing both the first and second input feature maps;
channel-wise multiply the first input feature map with the second attention feature map to yield a first post-processed input feature map;
channel-wise multiply the second input feature map with the first attention feature map to yield a second post-processed input feature map; and
perform elementwise addition of the first and second post-processed input feature maps to give the merged feature map such that channels with high activation in both the first and second input feature maps are preserved and enhanced.

2. The method of claim 1, wherein the multi-scale context aggregation module is further arranged to:
compute N atrous-convolution feature maps of the encoded final-stage feature map for N different dilation rates, respectively, for extracting the multi-scale contexts from the encoded final-stage feature map, where N≥2; and
compute the aggregated-context feature map, $s_N$, by a recursive procedure of computing $s_n = f_n(r_n \oplus s_{n-1})$ for $n \in \{1,2, \ldots, N\}$ where $r_n$ is an nth computed atrous-convolution feature map, $s_n$ is an nth intermediate result of the aggregated-context feature map, $s_0$ is a null feature map, $\oplus$ denotes elementwise summation and $f_n$ is an nth nonlinear function, wherein $(r_1, r_2, \ldots, r_N)$ forms a sequence of atrous-convolution feature maps arranged in a descending order of dilation rate such that local-scale contexts of the encoded final-stage feature map are allowed to be aggregated under guidance of global-scale contexts thereof, and wherein $f_1, f_2, \ldots, f_N$ are independently configured.

3. The method of claim 2, wherein $f_n$ is given by $f_n(x) = x + g_n(x)$ where x denotes an input feature map, $f_n(x)$ denotes an output of the nth nonlinear function with the input feature map, and $g_n(x)$ is a nonlinear component of $f_n(x)$.

4. The method of claim 3, wherein the multi-scale context aggregation module includes a plurality of bottleneck blocks for computing $f_1, f_2, \ldots, f_N$.

5. The method of claim 4, wherein an individual bottleneck block includes one or more convolutional layers.

6. The method of claim 1, wherein the pooling operation is either a first operation of computing an average value or a second operation of finding a maximum value.

7. The method of claim 1, wherein the attention layer employs a sigmoid function as an activation function.

8. The method of claim 1, wherein each data in the respective attention feature map is in a range of 0 and 1.

9. The method of claim 1, wherein:
the plurality of decoding stages comprises an initial decoding stage and one or more subsequent decoding stages, the one or more subsequent decoding stages including a last decoding stage;
the first input feature map of the initial decoding stage is the aggregated-context feature map, and the second input feature map thereof is, or is derived from, the encoded final-stage feature map;
the first input feature map of an individual subsequent decoding stage is the output map of a decoding stage immediately preceding the individual subsequent decoding stage, and the second input feature map thereof is, or is derived from, a feature map selected from the one or more encoded intermediate feature maps;

the output map of the last decoding stage is the segmentation map;

the decoding block of the individual decoding stage includes one or more convolutional layers; and the decoding block of the last decoding stage is realized as a 1×1 convolutional layer.

10. The method of claim 9, wherein the CNN further comprises:

one or more 1×1 convolutional layers, an individual 1×1 convolutional layer being arranged to derive the second input feature map of a decoding stage selected from the plurality of decoding stages, wherein the second input feature map of the selected decoding stage is derived from a corresponding feature map generated by the encoder by resampling the corresponding feature map such that the first and second input feature maps of the selected decoding stage have a same dimension.

11. The method of claim 1, wherein an individual encoding stage includes one or more convolutional layers.

12. A computer-implemented method for segmenting an input image into a segmentation map, the method comprising the step of running a convolutional neural network (CNN) to generate the segmentation map from the input image after the CNN is trained, wherein:

the CNN comprises:

an encoder arranged to encode the input image into an encoded final-stage feature map through plural encoding stages, generating one or more encoded intermediate feature maps before the encoded final-stage feature map is generated; and a decoder arranged to decode the encoded final-stage feature map according to, directly or indirectly, the one or more encoded intermediate feature maps, whereby the segmentation map is generated;

the decoder comprises a plurality of decoding stages, an individual decoding stage being arranged to receive first and second input feature maps to generate one output map, the first and second input feature maps each having a same dimension and a same number of channels, wherein the individual decoding stage comprises a merging module and a decoding block, the merging module being arranged to merge the first and second input feature maps to form a merged feature map, the decoding block being arranged to decode the merged feature map to give the output map; and the merging module is a channel-wise feature selection (CFS) module arranged to:

process the first and second input feature maps each with an individual cascade of a global pooling (GP) layer and an attention layer to yield first and second attention feature maps of dimension 1×1×C, respectively, wherein:

each of the first and second input feature maps has a dimension of W×H×C;

the GP layer performs a pooling operation on W×H data in each of C channels of a respective input feature map to yield a GP-output feature map of dimension 1×1×C; and the attention layer generates a respective attention feature map by determining an attention of each of the C channels according to the GP-output feature map such that a channel of higher activation among the C channels has a higher attention, the attention layer being either a fully connected layer or a 1×1 convolutional layer, a same set of weights being used in the attention layer of the individual cascade in processing both the first and second input feature maps channel-wise multiply the first input feature map with the second attention feature map to yield a first post-processed input feature map;

channel-wise multiply the second input feature map with the first attention feature map to yield a second post-processed input feature map; and perform elementwise addition of the first and second post-processed input feature maps to give the merged feature map such that channels with high activation in both the first and second input feature maps are preserved and enhanced.

13. The method of claim 12, wherein the pooling operation is either a first operation of computing an average value or a second operation of finding a maximum value.

14. The method of claim 12, wherein the attention layer employs a sigmoid function as an activation function.

15. The method of claim 12, wherein each data in the respective attention feature map is in a range of 0 and 1.

16. The method of claim 12, wherein:

the plurality of decoding stages comprises an initial decoding stage and one or more subsequent decoding stages, the one or more subsequent decoding stages including a last decoding stage;

the first input feature map of the initial decoding stage is the encoded final-stage feature map;

the first input feature map of an individual subsequent decoding stage is the output map of a decoding stage immediately preceding the individual subsequent decoding stage;

the second input feature map of an individual decoding stage is, or is derived from, a feature map selected from the one or more encoded intermediate feature maps;

the output map of the last decoding stage is the segmentation map;

the decoding block of the individual decoding stage includes one or more convolutional layers; and the decoding block of the last decoding stage is realized as a 1×1 convolutional layer.

17. The method of claim 12, wherein the CNN further comprises:

one or more 1×1 convolutional layers, an individual 1×1 convolutional layer being arranged to derive the second input feature map of a decoding stage selected from the plurality of decoding stages, wherein the second input feature map of the selected decoding stage is derived from a corresponding feature map generated by the encoder by resampling the corresponding feature map such that the first and second input feature maps of the selected decoding stage have a same dimension.

18. The method of claim 12, wherein an individual encoding stage includes one or more convolutional layers.

* * * * *